United States Patent [19]
Nguyen

[11] Patent Number: 5,363,347
[45] Date of Patent: Nov. 8, 1994

[54] VENDING TANNING TIMER

[76] Inventor: Hap Nguyen, 17461 Pleasant Ct., Fountain Valley, Calif. 92708

[21] Appl. No.: 201,411

[22] Filed: Feb. 24, 1994

[51] Int. Cl.⁵ .................. G04B 47/00; A61N 5/06
[52] U.S. Cl. .................... 368/10; 368/108; 607/88; 235/378
[58] Field of Search ........... 368/10, 107, 109; 128/375, 376, 395; 235/375, 377, 378, 380, 381, 382

[56] References Cited

U.S. PATENT DOCUMENTS

| | | | |
|---|---|---|---|
| 4,428,050 | 1/1984 | Pellegrino et al. | 364/413.3 |
| 4,600,009 | 7/1986 | Kramer et al. | 687/91 |
| 4,674,507 | 6/1987 | Basso | 607/91 |
| 4,729,375 | 3/1988 | Segers | 607/91 |
| 4,740,707 | 4/1988 | Thaw | 607/94 |
| 4,835,749 | 5/1989 | Welton | 368/10 |
| 4,989,600 | 2/1991 | Collier | 607/95 |

*Primary Examiner*—Vit W. Miska
*Attorney, Agent, or Firm*—John P. Halvonik

[57] ABSTRACT

A vending machine for controlling the use of a suntanning booth. The user inputs a card with a magnetic strip, bar code or the means for identifying the individual user into the machine to order a suntanning session. The program determines whether that user has used the tanning booth within a recent time period, if the user has, the booth is inoperable for that user. If the user has not used the booth recently, the machine is enabled and then coins or other money is then deposited to pay for the time period of suntanning. The system provides safeguards to limit the use of the tanning booth by identifying individual users and limiting the number of sessions each may have in a single time period.

2 Claims, 5 Drawing Sheets

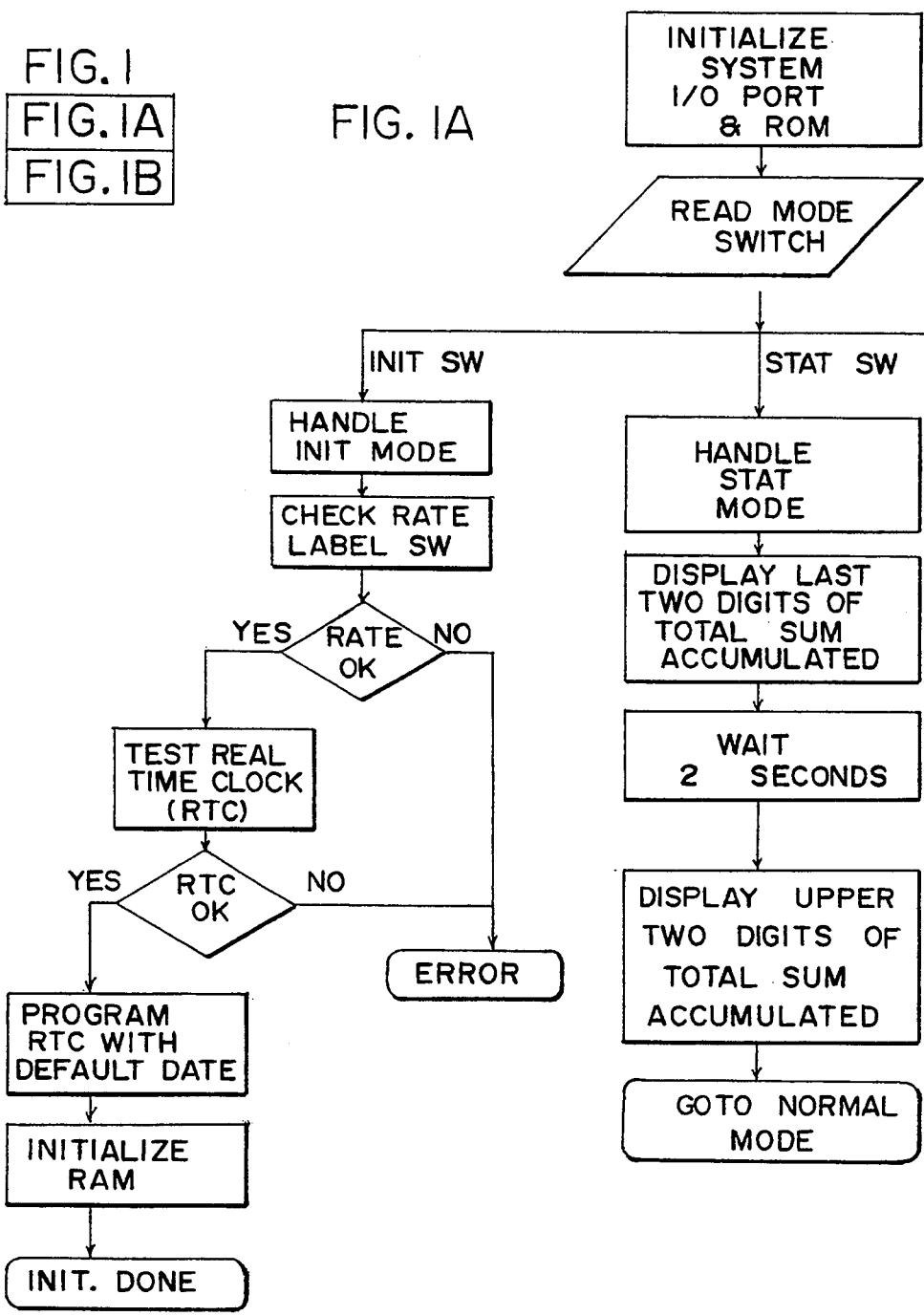

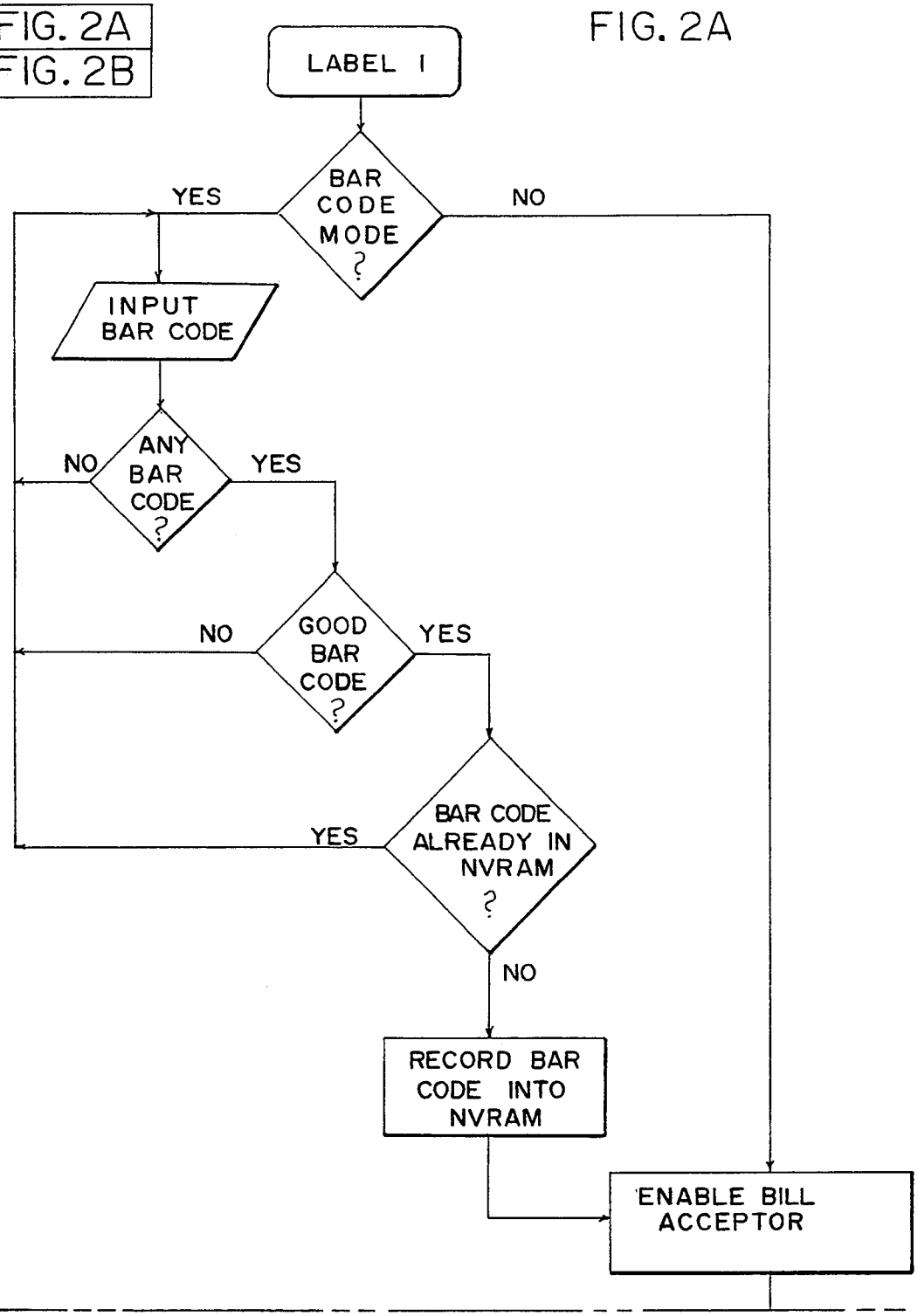

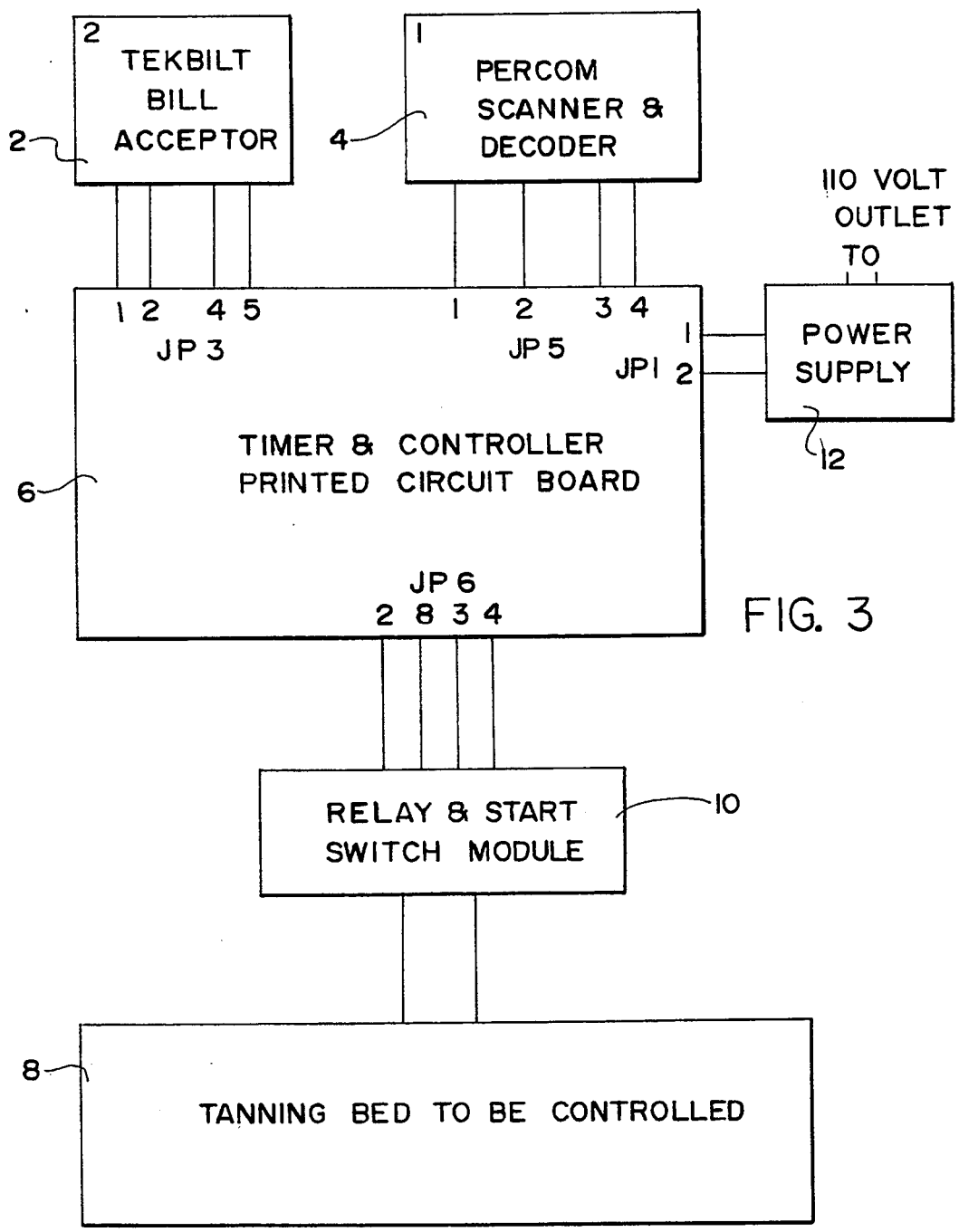

VENDING TANNING TIMER

FIELD OF INVENTION

BACKGROUND OF THE INVENTION

The invention relates to the field of vending machines and computer programs that operate them. The invention described herein controls the operation of the tanning booth by a card operated machine that controls the suntanning period as well as the number of times the suntanning booth may be used in a given period. One of the problems with tanning salons is that people like to use the tanning booth over and over again in a short period which may lead to problems with skin cancer etc. over the long term. It is believed that the invention will be useful in preventing this overexposure to the tanning lights by limiting the number of times anyone person may use the tanning booth.

It is thought that the invention will find utility by maintaining a network of subscribers to the tanning booth. Anyone who joins the network would be assigned their own ID number and a card that has this number encoded on it would be assigned to each person. When that person wishes to use the tanning booth he inserts the card to identify him or her as a member and the deposits the proper amount of money to correspond to a time period of tanning.

DESCRIPTION OF THE PRIOR ART

There are no card operated devices that applicant is aware of that control the operation of a suntanning booth including the timing of the suntanning session as well as the frequency of use of the suntanning booth.

SUMMARY OF THE INVENTION

The invention is a suntanning system that uses a card operated machine to control the operation of the suntanning booth. A computer stores in memory the identifying number of a user and prevents that user from using the tanning salon again within a certain time interval, for example: one day. The time period of the suntanning session is controlled by means of paper money or other forms of money that are deposited into the machine after the machine is activated by means of the card.

It is an object of the invention to provide a tanning salon that may be operated by the use of cards with magnetic strips that can identify individuals who are using the salon.

Another object of the invention is to provide a tanning salon that can identify the user through the use of identification numbers in order to limit the number of tanning sessions by an individual during a given time period.

Yet another objective is to provide a self regulated tannings salon that automatically controls the operation and admittance to the tanning salon and does not allow individuals to overexpose themselves.

Another objective is to provide a tanning salon that can be operated without human oversight by a plurality of subscribers to the tanning salon.

Other objectives of the invention will become apparent to those skilled in the art once the invention has been shown and described.

DESCRIPTION OF FIGURES

FIG. 3—Overall system

DESCRIPTION OF THE PREFERRED EMBODIMENT

Figure 1B:
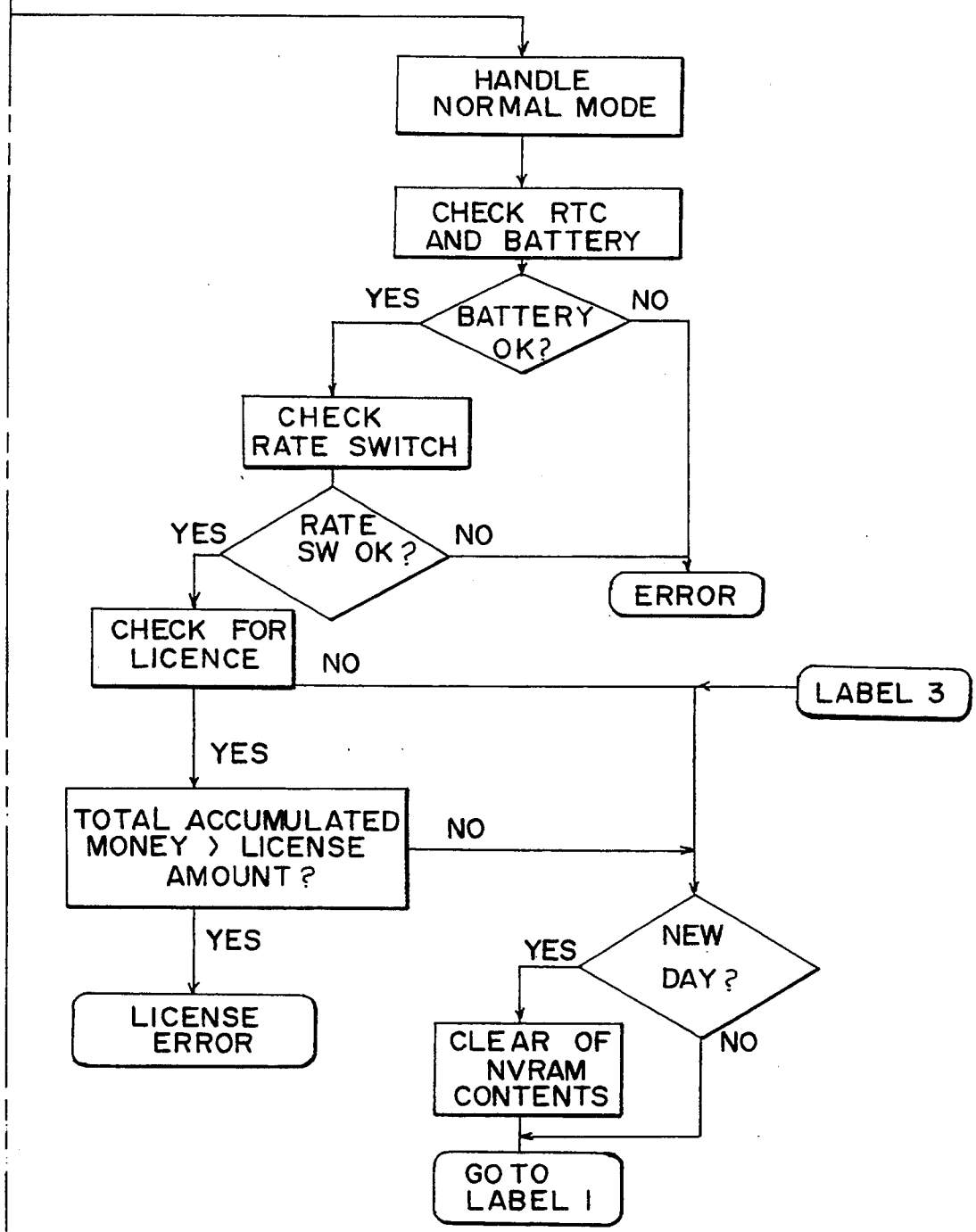
FIG. 1—First part of flow chart of program.

The overall system (FIG. 3) comprises a tanning booth with an illumination system 8, the booth would likely include a bank of lights, a bill acceptor 2 for accepting money, a card reader 4 for reading stored information from cards and a computer driven program that controls the operation of the lights, card acceptor and card reader. A printed circuit board 6 may be used to run the NVRAM and the computer program. A machine that houses both the card reader, bill acceptor and the printed circuit board may be constructed to house each of these elements. A power supply 12 is also thought necessary to power these elements.

The card reader reads magnetic strips on cards that may be inserted into a slot in the machine. There is a second slot on the machine for insertion of paper money or coins. This second slot is used by inserting the proper amount of money to pay for a certain time period for the tanning session i.e. the length of time of the tanning session. Appropriate elements may be used in conjunction with the second slot to insure that the proper money has been deposited.

It is preferred that the system be used in connection with a group of members who belong to the tanning salon. Each member would be issued a card with strips to identify each member. The identification strip on the cards may be e.g. a magnetic strip or may be a bar code. The code or strip corresponds to an ID number that identifies each member or subscriber of the system. Other means that would identify individual users by cards are possible without violating the spirit of the invention.

A card reading means 4 that corresponds to the type of strip (e.g. magnetic, optical, etc.) on the card is in the machine so that as a card is inserted into the card insertion slot the reading means may scan the card to determine the ID number and compares this number with those stored in memory of users who have used the tanning booth in a recent time period (e.g. one day).

It will be seen that the computer program in the system needs to keep track of at least four separate sets of date including: the current time also known as the real time (RTC); the elapsed time that the tanning booth has been on (the booth is not on continually but, when it is in use, the time elapsed needs to be accounted for); the set of identification numbers used by members that belong to the tanning salon and a temporary stored set of ID numbers that have been used during that time period (e.g. one day)stored in the NVRAM.

It is also an option that the system may keep track of an account balance for each particular ID number so that members of the tanning salon would not have to input money each time they use the machine. Another option is to have the computer keep track of the total amount of money accumulated that day, see FIG. 1 under the "handle stat" mode. This amount is then compared to the "license amount" and when it equals the license amount, the program may render the machine inoperable until a licensing payment is made.

Figure 2B:
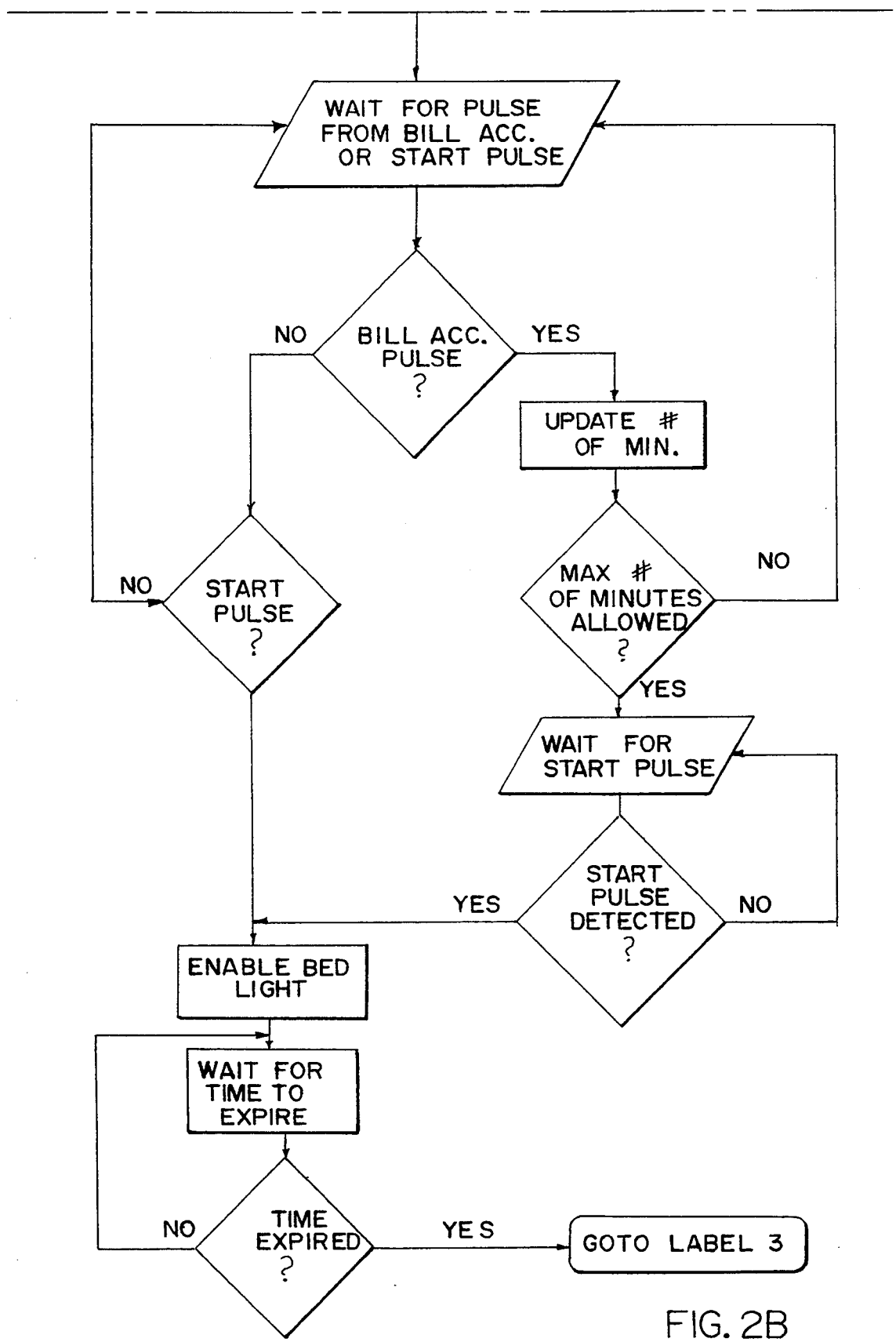
FIG. 2—Second part of flow chart.

It will be seen in FIG. 1 of the flow chart that upon activation of the system the I/O port and the RAM are initialized (or formatted) and, in FIG. 2, the process continues as the rate label sw is checked followed by the testing of the real time clock (RTC). If the clock is OK the RAM is initialized. This completes the initialization.

When in the handle normal mode the computer program checks the RTC and the battery. Upon confirmation that these are OK the rate switch is checked and the license is checked. The program then determines if there is enough money in the account for that number to allow for tanning.

At the start of each day the program will delete that data that needs to be deleted each day such as the ID numbers of those members who used the machine the day before. This data as well as data that needs to be stored more or less permanenty may be stored in non-volatile RAM (NVRAM) to thereby prevent such data from being deleted should the power to machine be disconnected. Non volatile RAM is typically powered by a battery.

Upon insertion of a member's card, the bar code on the card is read and determined if this corresponds to an ID number already in the NVRAM. If this bar code is not already in the NVRAM, the member has not used the tanning booth that day and the ID code is then inputted into the NVRAM. Upon completion of this process, the bill acceptor is enabled and the user may then input the appropriate amount of money into the machine in order to activate the tanning booth. As seen at label two, the bill acceptor will send a signal to the program that the proper amount of money has been inserted by sending a pulsed signal to the program.

When this signal is received, the program will consider the number of tanning minutes that the user has paid for and then keeps track of the time that has elapsed in the both. When this expires, the tanning lights are disabled.

While it is preferred that the system only use the card to enable the machine, with the member than having to insert paper or coin money into the machine to activate the booth, it is also possible that the program may keep track of an account balance for each ID number so that each member may keep an account for each number and this amount will be deducted from each time the member uses the booth.

After the card is inserted and the proper amount of money is inserted, the memory means of the machine stores the ID number in memory (NVRAM) for a certain time period, for example: one 24 hour day. At the end of this time period, this data is cleared and all ID numbers are removed from their storage in NVRAM. At this point, the start of a new day, anyone can again use the tanning booth upon inserting his card. The ID number will be stored in NVRAM only upon the actual use of the booth, not merely when one places the card in the reader slot. Also, if one pushes the start button before inserting the money, the tanning booth will not operate and the ID number will not be placed in memory.

Each time a card is read by the card reader the ID no. on that card is compared to those numbers already stored. If there is a match, the tanning booth is rendered inoperable. This is to prevent members from using the tanning both more than one time per day (or whatever time period is chosen). The computer will not enable the tanning booth unless a card is inserted with an ID number that has not been used recently. If the card is valid i.e. corresponds to a number that has not been used within that time period (e.g. the last 24 hours) then the tanning both will be operable and the member may insert the appropriate amount of money for activation of the tanning booth.

The memory would preferably be driven by a microprocessor with a non-volatile RAM printed circuit board. Other means are possible without violating the spirit of the invention. A clock (RTC) should be used in connection with the machine in order to provide proper length of tanning session as well as to keep track of the real time (necessary for deletion of the ID numbers on a daily basis.

At the end of each time period (e.g. one day), the memory will erase the ID numbers in the memory so that the when the next time period starts, every subscriber may use the machine again. The preferred time period would be 1 day but other time periods are possible without violating the spirit of the invention.

It is thought that the money slot would be of conventional design. A foreign currency acceptor may also be used. A safety option is possible where the if the machine determines that the clock is not running, the tanning booth is automatically shut down to prevent possible overexposure. Another signal may be given when the tanning session is completed.

As an option, it is possible to assign special numbers to preferred members to allow them multiple tanning sessions in the booth. This could be like for the salon manager who may be allowed two tanning sessions per day, etc. A rate switch in the program may be used to adjust the charges for a given length of tanning session. That is, there may be a discounted rate for purchasing a longer length of tanning session.

The "license amount" indicated in the flow chart is a predetermined amount of money that the system is allowed to take in until a licensing payment is due. It is contemplated that the machines will be distributed to franchisees for a licensing amount. The program will render the machine inoperable when a certain amount of money has been taken in. At this point, another licensing payment is due and, when it is made, the machine can be activated again by instructions sent by the franchiser.

I claim:

1. A tanning salon system for a plurality of subscribers, each subscriber having an identification code and a plurality of cards having different identification codes on each, said salon system comprising: tanning booth with means for emitting light, an activating means to render said booth operable, a vending stand having an insertion slot for said identification card and a money insertion slot, a card reader means in connection with said vending stand for reading said identification code on said card, a memory means for storing a plurality of said individual identification codes, a means for storing said identification codes in a second memory means for a short time period upon use of the tanning booth by those particular identification numbers, a means for comparing said identification code on said card with said codes in said second memory and for preventing the operation of said tanning booth in the event said identification code on said card matches one of said identification codes in said second memory, a means for recording time that tanning booth has been on, means for recording real time.

2. The system of claim 1 having a means for determining whether the amount of tanning time paid for exceeds the allowed tanning time for that particular identification number.

* * * * *